United States Patent
Narebski et al.

(10) Patent No.: US 8,211,416 B2
(45) Date of Patent: Jul. 3, 2012

(54) MASCARA COMPOSITION COMPRISING AN ETHYLENE/VINYL ACETATE COPOLYMER

(75) Inventors: Monique Narebski, La Blanc Mesnil (FR); Sophie Favre, Paris (FR)

(73) Assignee: Chanel Parfums Beaute, Neuilly-sur-Seine (FR)

( * ) Notice: Subject to any disclaimer, the term of this patent is extended or adjusted under 35 U.S.C. 154(b) by 324 days.

(21) Appl. No.: 12/520,674

(22) PCT Filed: Dec. 21, 2007

(86) PCT No.: PCT/EP2007/064509
§ 371 (c)(1),
(2), (4) Date: Jun. 22, 2009

(87) PCT Pub. No.: WO2008/077962
PCT Pub. Date: Jul. 3, 2008

(65) Prior Publication Data
US 2010/0092417 A1    Apr. 15, 2010

Related U.S. Application Data

(60) Provisional application No. 60/881,525, filed on Jan. 22, 2007.

(30) Foreign Application Priority Data

Dec. 22, 2006   (FR) ..................................... 06 11337

(51) Int. Cl.
*A61K 8/81* (2006.01)
*A61K 8/92* (2006.01)
*A61Q 1/10* (2006.01)

(52) U.S. Cl. ....................................................... 424/70.7
(58) Field of Classification Search ................... 424/70.7
See application file for complete search history.

(56) References Cited

U.S. PATENT DOCUMENTS

| | | | | |
|---|---|---|---|---|
| 5,389,363 A | * | 2/1995 | Snyder et al. | 424/70.7 |
| 6,083,491 A | * | 7/2000 | Mellul et al. | 424/63 |
| 2006/0024338 A1 | * | 2/2006 | Hegedus et al. | 424/401 |
| 2006/0099231 A1 | | 5/2006 | De La Poterie et al. | |

FOREIGN PATENT DOCUMENTS

| | | |
|---|---|---|
| EP | 0 530 084 A1 | 3/1993 |
| WO | WO 2005/112876 A1 | 12/2005 |

OTHER PUBLICATIONS

International Search Report dated Mar. 14, 2008.

* cited by examiner

*Primary Examiner* — Fereydoun G Sajjadi
*Assistant Examiner* — Michael B Pallay
(74) *Attorney, Agent, or Firm* — Young & Thompson

(57) ABSTRACT

The present invention relates to a mascara composition including a cosmetically acceptable aqueous medium, characterized in that it includes an oily phase including at least one ethylene/vinyl acetate copolymer, and at least one wax or a mixture of waxes in a certain weight ratio. The present invention also relates to a process for the care or make-up of eyelashes or eyebrows, characterized by the fact that a composition according to the invention is applied to the eyelashes or eyebrows. It also relates to the use of a composition according to the invention in order to obtain a make-up for filling and/or curling the eyelashes and/or a smooth and uniform deposition on the eyelashes.

20 Claims, No Drawings

MASCARA COMPOSITION COMPRISING AN ETHYLENE/VINYL ACETATE COPOLYMER

A subject of the present invention is a cosmetic mascara composition comprising an ethylene/vinyl acetate copolymer.

By mascara is meant a composition intended to be applied to the eyelashes: it can be an eyelash make-up composition, an eyelash make-up base, a composition to be applied over make-up, also known as a "top-coat", or also a cosmetic eyelash care composition. The mascara is more particularly intended for human eyelashes, but also false eyelashes.

Eyelash make-up compositions are generally constituted by a wax or mixture of wax(es) dispersed using at least one surfactant in an aqueous phase also containing polymers and pigments. It is generally through the qualitative and quantitative choice of waxes and polymers that the application specificities sought for make-up compositions, such as for example their fluidity, their coverage and/or their curling ability, are adjusted. Thus, it is possible to produce various compositions which, applied in particular to the eyelashes, induce varied effects of lengthening, curling and/or thickening (volumizing or loading effect) type.

The present invention aims more particularly to propose a useful mascara composition for producing a thick make-up of the eyelashes or eyebrows and in particular of the eyelashes, also called filling make-up.

It is known from the prior art that, the greater the solids content (supplied in part by an oily phase constituted for example by one or more waxes or one or more lipophilic polymers) in a composition, the greater will be the deposition of material on the eyelash and therefore the more volumizing will be the result obtained. Nevertheless, the increase in the solids content of a composition, such as an emulsion or dispersion, involves an increase in the consistency of the product obtained and therefore a delicate and difficult application to the eyelashes, as the product is thick, viscous, it forms a deposition with difficulty, unevenly and patchily, and the make-up thus obtained has a granular, not smooth, and unattractive appearance.

Another means of increasing the solids content is to incorporate solid particles such as fillers or pigments, but the increase in consistency also limits the maximum percentage of solids. Moreover, the use of solid particles in a large quantity does not encourage the uniform and smooth deposition, not only due to the consistency but also to the size of the introduced particles which gives the deposition a granular and non-smooth appearance. This is generally the case with so-called volumizing mascaras which are difficult to apply and give a non-uniform make-up.

It is therefore difficult to obtain a mascara composition comprising a high solids content and therefore a satisfactory volumizing effect, having an easy application and a uniform deposition.

Another means of obtaining more deposition of material on the eyelash and therefore obtaining volume is to multiply the number of layers deposited on the eyelash. However, the increase in the number of deposited layers leads to a non-uniform and patchy deposition, and the make-up thus obtained has a granular, non-smooth appearance; the make-up is not uniform and has an unattractive appearance.

It is therefore also difficult to obtain a mascara composition which is suitable for application in a greater number of layers and therefore a satisfactory volumizing effect, having an easy application and a uniform deposition.

Unexpectedly, it has thus been found that it is possible to prepare compositions allowing a thickening make-up of the eyelashes or eyebrows and a smooth and uniform deposition on said eyelashes or eyebrows thanks to the utilization, in these compositions, of an oily phase comprising an ethylene/vinyl acetate copolymer in an effective quantity and at least one wax or a mixture of waxes, wherein the weight ratio of the ethylene/vinyl acetate copolymer to the wax or mixture of waxes is comprised between 1:55 and 1:9.

Such a copolymer has already been disclosed as an additive in mascara compositions comprising water and waxes (U.S. Pat. No. 5,389,363 and US 2006/0024338). However, the inventors have discovered that adjusting the weight ratio of this copolymer to the waxes provides for unexpected effects, i.e. it allows conferring volume on the eyelashes while avoiding lumps.

A subject of the invention, according to one of its features, is therefore a mascara composition comprising a cosmetically acceptable aqueous medium, characterized in that it comprises an oily phase comprising at least one ethylene/vinyl acetate copolymer, and at least one wax or a mixture of waxes, wherein the weight ratio of the ethylene/vinyl acetate copolymer to the wax or mixture of waxes is comprised between 1:55 and 1:9.

The present invention also relates to a cosmetic process for the care or make-up of the eyelashes or eyebrows, characterized by the fact that a composition according to the invention is applied to said eyelashes or eyebrows.

It also relates to the use of a composition according to the invention in order to obtain a make-up for filling the eyelashes or eyebrows and in particular for the eyelashes and/or a smooth and uniform deposition on said eyelashes or eyebrows.

It also relates to the use of a composition according to the invention in order to obtain a make-up for curling the eyelashes.

By "filling" is meant within the meaning of the present invention the notion of a thick and volumizing make-up of the eyelashes or eyebrows.

The compositions according to the invention advantageously have a dry matter content greater than or equal to 37% by weight, preferably greater than or equal to 40% by weight, relative to the total weight of the composition.

The dry matter content can be measured in different ways. There can be mentioned for example oven-drying methods, the methods comprising drying by exposure to an infrared radiation as well as Karl Fischer water titration chemical methods. Preferably, the quantity of material, commonly called "dry extract" of the compositions according to the invention, is measured by heating the sample by infrared rays of a wavelength of 2 µm to 3.5 µm. The substances contained in said compositions which possess a high vapour pressure evaporate under the effect of this radiation. The measurement of the loss of weight of the sample makes it possible to determine "the dry extract" of the composition. These measurements are carried out using an LP 16 Mettler commercial infrared desiccator. This technique is fully described in the equipment documentation provided by Mettler.

The measurement procedure is the following:

Approximately 1 g of the composition is spread over a metal pan. The latter, after introduction into the desiccator, is subjected to a set-point temperature of 120° C. for one hour. The wet mass of the sample, corresponding to the initial mass, and the dry mass of the sample, corresponding to the mass after exposure to the radiation, are measured by means of a precision balance. The dry matter content is calculated as follows:

$$\text{Dry extract} = 100 \times (\text{dry mass}/\text{wet mass}).$$

The composition according to the invention comprises at least one ethylene/vinyl acetate copolymer and at least one wax or a mixture of waxes.

Ethylene/Vinyl Acetate Copolymer

By ethylene/vinyl acetate copolymer is meant within the meaning of the present invention a polymer obtained by polymerization of two or more monomers, including at least ethylene and vinyl acetate.

Preferably, an ethylene/vinyl acetate copolymer based only on ethylene and vinyl acetate monomers is used.

The vinyl acetate content present in the copolymer can advantageously vary between 5% and 55% by weight, relative to the total weight of the copolymer.

Preferably, a copolymer comprising between 10 and 45% by weight, and more preferably between 10 and 15% by weight or between 25 and 35% by weight of vinyl acetate, relative to the total weight of the copolymer, is used.

In particular, a copolymer the vinyl acetate level of which is approximately 13% by weight of vinyl acetate, relative to the total weight of the copolymer, is used.

As a variant, a copolymer the vinyl acetate content of which is approximately 28% by weight of vinyl acetate, relative to the total weight of the copolymer, is used.

Moreover, the ethylene content of the copolymer can advantageously vary between 45 and 95% by weight, relative to the total weight of the copolymer.

The ethylene/vinyl acetate copolymer of the invention can be prepared by any standard polymer preparation process.

It is generally present in a sufficient quantity in the composition to avoid the formation of lumps during application of the formula to the eyelashes.

The quantity of ethylene/vinyl acetate copolymer can thus be adjusted according to the level of waxes present in the composition of the invention, provided that the weight ratio of the ethylene/vinyl acetate copolymer to the wax or mixture of waxes is comprised between 1:55 and 1:9.

The weight ratio of the ethylene/vinyl acetate copolymer to the wax or mixture of waxes in the composition of the invention is preferably comprised between 1:55 and 1:15 and more preferably between 1:50 and 1:20.

When the weight ratio of the ethylene/vinyl acetate copolymer to the wax or mixture of waxes in the composition of the invention is less than 1:55, the quantity of ethylene/vinyl acetate copolymer present in the composition of the invention is not adequate and the composition has a non-uniform deposition, i.e. lumps, when it is applied to the eyelashes.

When the weight ratio of the ethylene/vinyl acetate copolymer to the wax or mixture of waxes in the composition of the invention is greater than 1:9, the composition of the invention has the drawback of being very fluid and not forming an adequate deposition on the eyelashes.

The compositions of the invention preferably have a wax content less than or equal to 30% by weight and preferably greater than 1% by weight, relative to the total weight of the composition.

In a preferred embodiment of the invention, an ethylene/vinyl acetate copolymer dispersed beforehand in a mixture of waxes is used.

This has the advantage of reducing the melting point of the copolymer, which makes it possible to reduce the heating temperature for the preparation of the composition of the invention.

The waxes used for the predispersion of the copolymer of the invention can be chosen from those which are mentioned below. Preferably, the waxes used in order to predisperse the polymer are chosen from synthetic wax, microcrystalline wax or their mixture.

In particular, a pre-mixture of copolymer in waxes comprising 80% by weight ethylene/vinyl acetate copolymer, in which the percentage of vinyl acetate is 13% by weight relative to the total weight of the copolymer, can be used, the copolymer being pre-dispersed in a mixture of waxes comprising 15% by weight microcrystalline wax and 5% by weight synthetic wax sold under the name Cérylène B72® by the company Baerlocher.

Wax

The composition according to the invention comprises a wax or a mixture of waxes. The wax considered within the framework of the present invention is generally a lipophilic compound, solid at ambient temperature (25° C.), with reversible solid/liquid change of state, having a melting point greater than or equal to 30° C. which can range up to 120° C. By raising the wax to the liquid state (melting), it is possible to make it miscible with oils and to form a microscopically uniform mixture, but on returning the temperature of the mixture to ambient temperature, a recrystallization of the wax from the oils in the mixture is achieved. In particular, the waxes according to the invention can have a melting point greater than approximately 45° C. or, more preferably, greater than or equal to 50° C. and in particular greater than or equal to 55° C. The melting point of the wax can be measured using a differential scanning calorimeter (D.S.C.), for example the calorimeter sold under the name MDSC 2929 by the company TA Instruments.

The measurement procedure is the following:

A sample of 5 mg of product arranged in a crucible is subjected to a first rise in temperature from 0° C. to 120° C., at a heating rate of 10° C./minute, then cooled from 120° C. to 0° C. at a cooling rate of 10° C./minute and finally subjected to a second rise in temperature from 0° C. to 120° C. at a heating rate of 5° C./minute. For the second rise in temperature, the variation in the difference in power absorbed by the empty crucible and by the crucible containing the sample of product is measured according to the temperature. The melting point of the compound is the value of the temperature corresponding to the tip of the peak of the curve representing the variation in the difference in power absorbed according to the temperature.

The waxes capable of being used in the compositions according to the invention can be chosen from waxes which are solid and rigid at ambient temperature, of animal, vegetable, or mineral origin or synthetic waxes and their mixtures. It is in particular possible to use hydrocarbon waxes such as beeswax, lanolin wax, lemon wax, orange wax, and Chinese insect waxes; rice wax, carnauba wax, candellila wax, ouricurry wax, Japan wax, berry wax, shellac wax and sumac wax; montan wax, microcrystalline waxes, paraffins and ozokerite; polyethylene and polymethylene waxes, waxes obtained by Fisher-Tropsch synthesis and waxy copolymers as well as their esters. There can also be mentioned the waxes obtained by catalytic hydrogenation of animal or vegetable oils having linear or branched $C_8$-$C_{32}$ fatty chains. Among the latter, there can in particular be mentioned hydrogenated jojoba oil, isomerized jojoba oil such as isomerized partially hydrogenated trans jojoba oil, produced or sold by the company Desert Whale under the trade name ISO-JOJOBA-50®, hydrogenated sunflower oil, hydrogenated ricin oil, hydrogenated copra oil and hydrogenated lanolin oil, di-(trimethylol-1,1,1 propane) tetrastearate sold under the name HEST 2T-4S® by the company HETERENE, and di-(trimethylol-1,1,1 propane) tetrabehenate sold under the name HEST 2T-4B® by the company HETERENE.

There can also be mentioned silicone waxes and siliconized modified waxes such as for example siliconized candellila wax, or also fluorinated waxes.

The composition according to the invention can comprise a total waxes content ranging from 5 to 50% by weight relative to the total weight of the composition, preferably from 10 to 35% by weight, more particularly from 15 to 30% by weight, relative to the total weight of the composition.

Oily Phase

As indicated previously, the oily phase of the composition according to the invention comprises at least one ethylene/vinyl acetate copolymer and at least one wax or a mixture of waxes.

By "oily phase" is meant within the meaning of the invention a phase composed of one or more non-aqueous bodies which are liquid or solid at ambient temperature (25° C.), generally compatible with each other, such as waxes, pasty fatty substances, oils, oils thickened by a structuring agent and their mixtures. The surfactants as described below do not form part of the oily phase within the meaning of the invention.

Pasty Fatty Substances

The oily phase of the composition according to the invention can comprise one or more pasty fatty substances. The pasty fatty substances can be chosen from silicone gums. There can be mentioned in particular dimethiconol sold under the name DC 1501® by the company Dow Corning.

Oils

The oily phase of the composition according to the invention can also comprise one or more oils, chosen from volatile oils, non-volatile oils, and their mixtures.

The oil or oils can be present in the composition according to the invention at a level ranging from 0.1% to 60% by weight, preferably from 0.1% to 30% by weight, relative to the total weight of the composition.

By "volatile oil" is meant within the meaning of the invention an oil capable of evaporating on contact with the skin or keratin fibre in less than an hour, at ambient temperature and atmospheric pressure. The volatile oils of the invention are volatile cosmetic oils, liquid at ambient temperature, having a vapour pressure other than zero, at ambient temperature and atmospheric pressure, ranging in particular from 0.13 Pa to 40,000 Pa ($10^{-3}$ to 300 mm of Hg), in particular ranging from 1.3 Pa to 13,000 Pa (0.01 to 100 mm of Hg), and more particularly ranging from 1.3 Pa to 1300 Pa (0.01 to 10 mm of Hg).

By "non-volatile oil" is meant an oil remaining on the skin or the keratin fibre at ambient temperature and atmospheric pressure for at least one hour and having in particular a vapour pressure of less than $10^{-3}$ mm of Hg (0.13 Pa).

These oils can be hydrocarbon oils, siliconized oils, fluorinated oils, or their mixtures.

Volatile Oils

By "hydrocarbon oil" is meant an oil containing mainly hydrogen and carbon atoms and optionally oxygen, nitrogen, sulphur and phosphorus atoms. The volatile hydrocarbon oils can be chosen from the hydrocarbon oils having 8 to 16 carbon atoms, and in particular the $C_8$-$C_{16}$ branched alkanes such as the $C_8$-$C_{16}$ isoalkanes of petroleum origin (also called isoparaffins) such as isododecane (also called 2,2,4,4,6-pentamethylheptane), isodecane, isohexadecane, and for example the oils sold under the trade names Isopar® or Permethyl®, the branched $C_8$-$C_{16}$ esters, isohexyl neopentanoate, and their mixtures. Other volatile hydrocarbon oils such as petroleum distillates, in particular those sold under the name Shell Soit® by the company SHELL, can also be used. The hydrocarbon volatile oil is preferably chosen from those having 8 to 16 carbon atoms.

It is also possible to use as volatile oils volatile silicones, such as for example volatile linear or cyclic silicone oils, in particular those having a viscosity <8 centistokes (8 $10^{-8}$ m²/s), and having in particular from 2 to 7 silicon atoms, these silicones optionally comprising alkyl or alkoxy groups having 1 to 10 carbon atoms.

Non-volatile Oils

The composition can comprise, as a variant or in addition, at least one non-volatile oil, in particular chosen from non-volatile hydrocarbon and/or siliconized and/or fluorinated oils.

Structuring Agent

The structuring agent of the oil(s), if present, can be chosen from semi-crystalline polymers, lipophilic gelling agents and their mixtures.

By polymer is meant compounds comprising at least two, preferably at least 3 units and more especially at least 10 repetition units. By "semi-crystalline polymer" is meant polymers comprising a crystallizable part, a crystallizable pendent chain or a crystallizable sequence in the skeleton, and an amorphous part in the skeleton and having a first-order reversible phase change temperature, in particular melting point (solid-liquid transition). When the crystallizable part is in the form of a crystallizable sequence of the polymer skeleton, the amorphous part of the polymer is in the form of an amorphous sequence; the semi-crystalline polymer is in this case a sequenced copolymer for example of the diblock, triblock or multiblock type, comprising at least one crystallizable sequence and at least one amorphous sequence. By "sequence" is generally meant at least 5 identical repetition units. The crystallizable sequence or sequences are then of a different chemical nature from the amorphous sequence or sequences.

The semi-crystalline polymer has a melting point greater than or equal to 30° C. (in particular ranging from 30° C. to 80° C.), preferably ranging from 30° C. to 60° C. This melting point is a first order state change temperature. This melting point can be measured by any known method and in particular using a differential scanning calorimeter (D.S.C).

The semi-crystalline polymer can be chosen from sequenced copolymers comprising at least one crystallizable sequence and at least one amorphous sequence, the homopolymers and the copolymers carrying at least one crystallizable side chain per repetition unit, and their mixtures. Such polymers are described for example in document EP 1396259. According to a more particular embodiment of the invention, the polymer originates from a monomer with a crystallizable chain chosen from the saturated $C_{14}$ to $C_{22}$ alkyl(meth)acrylates. By way of a particular example of a structuring semi-crystalline polymer which can be used in the composition according to the invention, there can be mentioned the Intelimer® products of the company Landec described in the "Intelimer® polymers" brochure, Landec IP22 (Rev. 4-97). These polymers are in solid form at ambient temperature (25° C.). They carry crystallizable side chains.

The gelling agents which can be used in the compositions according to the invention can be organic or mineral, polymeric or molecular lipophilic gelling agents. As mineral lipophilic gelling agents there can be mentioned optionally modified clays such as hectorites modified by a $C_{10}$ to $C_{22}$ fatty acid ammonium chloride, such as hectorite modified by di-stearyl di-methyl ammonium chloride such as, for example, that sold under the name Bentone 38V® by the company ELEMENTIS. There can also be mentioned the optionally surface-treated hydrophobic pyrogenic silica, the size of the particles of which is less than 1 µm. It is in fact possible to chemically modify the surface of the silica, by chemical reaction causing a reduction in the number of silanol groups present on the surface of the silica. It is in particular possible to substitute silanol groups by hydrophobic groups: a hydrophobic silica is then obtained. The hydrophobic groups can be:

- trimethylsiloxyl groups, which are in particular obtained by treatment of pyrogenic silica in the presence of hexamethyldisilazane. Silicas treated thus are called "Silica silylate" according to the CTFA (6th edition, 1995). They are sold, for example, under the names Aerosil R812® by the company DEGUSSA, and CAB-O-SIL TS-530® by the company CABOT,
- dimethylsilyloxyl or polydimethylsiloxane groups, which are in particular obtained by treatment of pyrogenic silica in the presence of polydimethylsiloxane or dimethyldichlorosilane. Silicas treated thus are called "Silica dimethyl silylate" according to the CTFA (6th edition, 1995). They are sold, for example, under the names Aerosil R972® and Aerosil R974® by the company DEGUSSA, or CAB-O-SIL TS-610® and CAB-O-SIL TS-720® by the company CABOT.

Hydrophobic pyrogenic silica has in particular a particle size which can range from nanometric to micrometric, for example ranging from approximately 5 to 200 nm.

Polymeric organic lipophilic gelling agents are for example polyamide-type polycondensates resulting from the condensation between (a) at least one acid chosen from the dicarboxylic acids comprising at least 32 carbon atoms such as the dimeric fatty acids and (P) an alkylene diamine and in particular ethylene diamine, in which the polyamide polymer comprises at least one esterified or amidated terminal carboxylic acid group with at least one monoalcohol or monoamine comprising 12 to 30 linear and saturated carbon atoms, and in particular, ethylenediamine/stearyl dilinoleate copolymers as sold under the name Uniclear 100 VG Sylvaclear® by the company ARIZONA CHEMICAL; polyamides such as those identified by the INCI name polyamide-3 and in particular the polymers SYLVACLEAR AF 1900V® and PA 1200V® sold by the company ARIZONA CHEMICAL as well as those identified by the INCI name "Ethylenediamine/Hydrogenated Dimer Dilinoleate Copolymer Bis-Di-C14-18 Alkyl Amide" and sold under the trade name SYLVACLEAR A200V® or SYLVACLEAR A2614V® by the company ARIZONA CHEMICAL; galactommanans comprising one to six, and in particular two to four, hydroxyl groups per monosaccharide, substituted by a saturated or unsaturated alkyl chain, such as guar gum alkylated by $C_1$ to $C_6$, and in particular $C_1$ to $C_3$ alkyl chains and their mixtures. Sequenced copolymers of "diblock", "triblock" or "radial" type of the polystyrene/polyisoprene, polystyrene/polybutadiene type such as those sold under the name Luvitol HSB® by the company BASF, of the polystyrene/copoly(ethylene-propylene) type such as those sold under the name Kraton® by the company SHELL CHEMICAL CO or also of the polystyrene/copoly(ethylene-butylene) type, mixtures of triblock and radial (star) copolymers in isododecane such as those sold by the company PENRECO under the name Versagel® such as for example butylene/ethylene/styrene triblock copolymer and ethylene/propylene/styrene star copolymer mixtures in the Versagel® series MN, MC, ME and MP; fatty acid polyesters such as the glyceryl behenate/eicosadioate sold under the name Nomcort HK-G® by the company Nisshin Oil or glyceryl behenate/isostearate/eicosadioate sold under the name Nomcort SG® by the company Nisshin Oil; and fatty acid esters such as methyl palmitate, methyl stearate, or methyl behenate.

Among the lipophilic gelling agents which can be used in the compositions according to the invention, there can also be mentioned the dextrin and fatty acid esters, such as the dextrin palmitates, in particular those sold under the names Rheopearl TL® or Rheopearl KL® by the company CHIBA FLOUR.

The oily phase of the composition of the invention can represent 5% to 60% by weight relative to the total weight of the composition, preferably 10% to 50% and more preferably 15% to 30% by weight relative to the total weight of the composition.

Cosmetically Acceptable Aqueous Medium

The cosmetically acceptable aqueous medium of the composition according to the invention can essentially be constituted by water. It can also comprise a mixture of water and water-miscible solvents (miscibility in water greater than 50% by weight at 25° C.) such as lower monoalcohols having 1 to 5 carbon atoms such as ethanol, isopropanol, glycols having 2 to 8 carbon atoms such as propylene glycol, ethylene glycol, 1,3-butylene glycol, dipropylene glycol, $C_3$-$C_{64}$ ketones, $C_2$-$C_4$ aldehydes and their mixtures.

The aqueous medium (water and optionally the water-miscible solvent) can be present at a level ranging from 0.1% to 95% by weight relative to the total weight of the composition, preferably ranging from 10% to 65% by weight relative to the total weight of the composition.

Emulsifying System

According to the invention, an emulsifying system chosen appropriately is used in order to obtain a wax-in-water emulsion.

The compositions according to the invention can contain emulsifying surfactants present in particular in a proportion ranging from 0.1 to 40% and more preferably from 1% to 10% by weight, relative to the total weight of the composition.

The surfactants used within the framework of the present invention can be anionic, cationic, non-ionic or amphoteric.

However, generally, the choice of at least one anionic surfactant is favoured.

As representative of anionic surfactants suitable for the invention, there can more particularly be mentioned $C_{16}$-$C_{30}$ fatty acid salts in particular those derived from amines, such as triethanolamine stearate and/or aminomethyl-1,3-propanediol stearate. The latter is generally obtained by simply mixing stearic acid with triethanolamine and/or aminomethyl-1,3-propanediol.

Generally, the compositions according to the invention can contain 0.1 to 30% by weight, in particular 0.5 to 20% by weight or even 1 to 10% by weight surfactant relative to the total weight of the composition.

The composition according to the invention can comprise, as a variant or in addition, at least one non-ionic or amphoteric surfactant. Reference may be made to the document "Encyclopedia of Chemical Technology, KIRK-OTHMER", volume 22, p. 333-432, 3rd edition, 1979, WILEY, for the definition of the (emulsifying) properties and functions of surfactants. A preferred non-ionic emulsifier is a polyalcoxylated glycerol ester such as PEG-15 glyceryl stearate which may be obtained from NIKKO CHEMICALS under the trade name Emalex® GM-15.

Cellulose Polymer

According to an advantageous embodiment, the composition according to the invention comprises a cellulose polymer in addition to the ethylene/vinyl acetate copolymer.

The cellulose polymer is preferably film-forming. By "film-forming" polymer is meant a polymer capable of forming, alone or in the presence of a film-forming auxiliary, a continuous film adhering to a support, in particular to keratin materials, and preferably a cohesive film.

By cellulose polymer is meant cellulose or a cellulose derivative. The cellulose polymer can be chosen from the alkylcelluloses such as methylcellulose, ethylcellulose, hydroxyalkylcelluloses such as hydroxyethylcellulose, hydroxypropylcellulose, ethylhydroxyethylcellulose, carboxyalkylcelluloses such as carboxymethylcellulose and their mixtures.

The cellulose polymer can be present in the composition according to the invention at a dry matter level ranging from 0.1% to 30% by weight relative to the total weight of the composition, preferably from 0.5% to 20% by weight and more preferably from 1% to 10% by weight, relative to the total weight of the composition.

Film-forming Polymer of Natural Origin

According to another advantageous embodiment, the composition according to the invention comprises, apart from the ethylene/vinyl acetate copolymer, an optionally modified film-forming polymer of natural origin.

Among the optionally modified film-forming polymers of natural origin there can be mentioned in particular gum arabic, guar gum, xanthan derivatives, karaya gum; alginates and carrageenins; shellac resin, sandarac gum, dammar resins, elemi gums, copal resins; deoxyribonucleic acid; mucopolysaccharides such as hyaluronic acid, chondroitin sulphates, their derivatives and their mixtures. Preferably, gum arabic is used.

The optionally modified film-forming polymer of natural origin can be present in the composition according to the invention at a dry matter level ranging from 0.1% to 30% by weight relative to the total weight of the composition, preferably 0.5% to 20% by weight, and more preferably 1% to 10% by weight relative to the total weight of the composition.

Cationic Polyquaternium-Type Film-forming Polymer

According to another advantageous embodiment, the composition according to the invention comprises, apart from the ethylene/vinyl acetate copolymer, a cationic polyquaternium-type film-forming polymer.

Among the cationic polyquaternium-type film-forming polymers there can be mentioned in particular:

cationic polyquaternium-10-type polymers sold under the name Polymer JR400 by the company Amerchol, polyquaternium-11 sold under the name Luviquat PQ11PN (BASF) or Gafquat 734 (ISP), polyquaternium-24 sold under the name Mirustyl CP (Croda), polyquaternium-37 sold under the name Syntran PC5320 (Interpolymer), polyquaternium-46 sold under the name Luviquat Hold (BASF), polyquaternium-55 sold under the name Styleze W-10 (ISP), or their mixtures. Preferably, polyquaternium-10 is used.

The cationic polyquaternium-type film-forming polymer can be present in the composition according to the invention at a level of dry matter ranging from 0.1% to 30% by weight relative to the total weight of the composition, preferably 0.5% to 20% by weight, and more preferably 1% to 10% by weight relative to the total weight of the composition.

The composition according to the invention can comprise, apart from the optional cellulose polymer and/or the film-forming polymer of natural origin and/or the cationic polyquaternium-type film-forming polymer, an additional film-forming polymer.

Additional Film-forming Polymer

The additional film-forming polymer can be present in the composition according to the invention at a level of dry matter ranging from 0.1% to 60% by weight relative to the total weight of the composition, preferably 0.5% to 40% by weight, and more preferably 1% to 30% by weight.

Among the additional film-forming polymers which can be used in the composition of the present invention there can be mentioned synthetic polymers of radical type or polycondensate type, and their mixtures.

By radical film-forming polymer is meant a polymer obtained by polymerization of, in particular ethylenically, unsaturated monomers, each monomer being capable of homopolymerizing (unlike polycondensates).

The film-forming polymers of radical type can be in particular vinyl polymers or copolymers, in particular acrylic polymers.

The vinyl film-forming polymers can result from the polymerization of ethylenically unsaturated monomers containing at least one acid group and/or esters of these acid monomers and/or amides of these acid monomers. As monomer bearing an acid group there can be used ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

Among the film-forming polycondensates there can be mentioned polyurethanes, polyester, polyester amides, polyamides, epoxyester resins and polyureas.

The composition can moreover comprise a hydrosoluble film-forming polymer chosen from:

proteins, such as proteins of vegetable origin such as wheat, soya proteins; proteins of animal origin such as keratins, for example keratin hydrolysates and sulphonic keratins;

anionic, cationic, amphoteric or non-ionic chitin or chitosan polymers;

vinyl polymers, such as polyvinylpyrrolidones, methylvinyl ether and malic anhydride copolymers, vinyl acetate and crotonic acid copolymer and vinylpyrrolidone and vinyl acetate copolymers; vinylpyrrolidone and caprolactam copolymers; polyvinyl alcohol.

According to an embodiment of the composition according to the invention, the additional film-forming polymer can be a polymer solubilized in a liquid organic medium of the composition comprising oils or organic solvents such as those described below (it can then be said that the film-forming polymer is a liposoluble polymer).

By way of example of a liposoluble polymer there can be mentioned vinyl ester copolymers (the vinyl group being directly linked to the oxygen atom of the ester group and the vinyl ester having a saturated linear or branched hydrocarbon radical having 1 to 19 carbon atoms, linked to the carbonyl of the ester group) and at least one other monomer which can be a vinyl ester (different from the vinyl ester already present), an $\alpha$-olefin (having 8 to 28 carbon atoms), an alkylvinyl ether (the alkyl group of which comprises 2 to 18 carbon atoms), or an allyl or methallyl ester (having a saturated linear or branched hydrocarbon radical having 1 to 19 carbon atoms, linked to the carbonyl of the ester group).

As liposoluble film-forming polymers which can be used in the invention, there can also be mentioned polyalkylenes and in particular $C_2$-$C_{20}$ homo- and copolymers of alkenes, such as polybutene, alkylcelluloses with a linear or branched, saturated or unsaturated $C_1$-$C_8$ alkyl radical, such as ethylcellulose and propylcellulose, copolymers of vinylpyrrolidone (VP) and in particular copolymers of vinylpyrrolidone and of $C_2$-$C_{40}$ and more preferably $C_3$-$C_{20}$ alkene. As an example of a VP copolymer which can be used in the invention there can be mentioned copolymers of VP/vinyl acetate, VP/ethyl methacrylate, butylated Polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The film-forming polymer can also be present in the composition in the form of particles dispersed in an aqueous phase or in a non-aqueous solvent phase (liquid organic medium of the composition), generally called a latex or pseudolatex. The techniques for preparing these dispersions are well known to one skilled in the art.

Aqueous dispersions of film-forming polymers that can be used are the acrylic dispersion sold under the names Syntran 5760® by the company Interpolymer, Aquamere H-1511® by the company HYDROMER; the sulphopolyesters sold under the brand name Eastman AQ® by the company Eastman Chemical Products; and their mixtures.

The composition according to the invention can comprise a plasticizer that encourages the formation of a film with the film-forming polymer. Such a plasticizer can be chosen from all the compounds known to a person skilled in the art as being capable of fulfilling the desired function.

The claimed compositions can also contain ingredients commonly used in the field of mascaras.

Additives

The composition according to the invention can also comprise at least one colorant such as powdery colorants, liposoluble colorants and water-soluble colorants. This dyestuff can be present at a level ranging from 0.01% to 30% by weight relative to the total weight of the composition.

The powdery dyestuffs can be chosen from pigments and nacres.

The pigments can be white or coloured, mineral and/or organic, coated or uncoated. Among mineral pigments there can be mentioned titanium dioxide, optionally surface-treated, zirconium, zinc or cerium oxides, and also iron or chromium oxides, manganese violet, ultramarine blue, chromium hydrate and ferric blue.

Among organic pigments there can be mentioned carbon black, pigments of D&C type, and lakes based on cochineal carmine, barium, strontium, calcium and/or aluminium.

The nacres can be chosen from white nacreous pigments such as mica coated with titanium or bismuth oxychloride, coloured nacreous pigments such as titanium mica with iron oxides, titanium mica with, especially, ferric blue or chromium oxide, titanium mica with an organic pigment of the abovementioned type, and also nacreous pigments based on bismuth oxychloride.

Liposoluble colorants are, for example, Sudan Red, D&C Red 17, D&C Green 6, p-carotene, soybean oil, Sudan Brown, D&C Yellow 11, D&C Violet 2, D&C Orange 5, quinoline yellow and annatto. Hydrosoluble colorants are for example beetroot juice, methylene blue, ponceau disodium salt, alizarine green disodium salt, quinoleine yellow, amaranth trisodium salt, tartrazine disodium salt, rhodamine monosodium salt, fuchsine disodium salt, xanthophyll.

The composition according to the invention may also comprise at least one filler chosen from those well known to one skilled in the art and commonly used in cosmetic compositions. The fillers can be mineral or organic, lamellar or spherical. There can be mentioned talc, mica, silica, kaolin, polyamide powders such as Nylon® (Orgasol from Atochem), poly-β-alanine and polyethylene powders, tetrafluoroethylene polymer powders such as Teflon®, lauroyllysine, starch, boron nitride, acrylic powders such as Polytrap® (Dow Corning), polymethyl methacrylate particles and silicone resin microbeads (Tospearls® from Toshiba, for example), precipitated calcium carbonate, magnesium carbonate and hydrocarbonate, hydroxyapatite, hollow silica microspheres (SILICA BEADS® from MAPRECOS), glass or ceramic microcapsules, metal soaps derived from organic carboxylic acids having 8 to 22 carbon atoms, preferably from 12 to 18 carbon atoms, for example zinc, magnesium or lithium stearates, zinc laurate and magnesium myristate, cellulose microbeads (Cellulobeads® sold by the company LCW) and carbon black Cellulobeads® sold by the company LCW, or black iron oxide.

The fillers may represent from 0.1% to 25% and more preferably from 1% to 20% by weight of the total weight of the composition.

The composition of the invention may also comprise any additive customarily used in cosmetics, such as antioxidants, preservatives, fragrances, neutralizers, hydrophilic gelling agents, thickeners, vitamins, fibres and their mixtures.

The hydrosoluble gelling polymer can be present in the composition according to the invention at a level of dry matter ranging from 0.01% to 60% by weight, preferably 0.5% to 40% by weight, more preferably 1% to 30% by weight, even 5 to 20% by weight relative to the total weight of the composition.

By "fibre" is to be understood an object of length L and diameter D such that L is much greater than D, D being the diameter of the circle in which the cross section of the fibre is inscribed. In particular, the ratio L/D (or form factor) is chosen in the range from 3.5 to 2500, preferably from 5 to 500 and more preferably from 5 to 150. In particular, the fibres have a length ranging from 1 μm to 10 mm, preferably from 0.1 mm to 5 mm and more preferably from 0.3 mm to 3 mm.

The fibres which can be used in the composition of the invention can be chosen from rigid or non-rigid fibres, and may be of synthetic or natural, mineral or organic origin.

As fibres that can be used in the composition according to the invention, there can be mentioned non-rigid fibres such as polyamide (Nylon®) and in particular Nylon-6 fibres such as those sold under the trade name 3D-1mm® or 10D-2 mm® by the company Toray. Fibres with carbon black can also be mentioned, in particular those sold under the name NFCB® by the company Daito Kasei and in particular those with a triangular section. Sodium polyacrylate fibres can also be mentioned, in particular those sold under the name Oasis® by the company Technical Absorbents. Silica fibres can also be mentioned.

A person skilled in the art will of course take care to choose any supplementary additives and/or their quantity in such a way that the advantageous properties of the composition according to the invention are not, or are not substantially, altered by the envisaged addition.

The composition according to the invention is preferably a mascara. The composition according to the invention can be packaged in a container delimiting at least one compartment which houses said composition, said recipient being closed by a closure element.

The container is preferably combined with an applicator, especially in the form of a brush comprising an arrangement of bristles held by a twisted wire. Such a twisted brush is described in particular in U.S. Pat. No. 4,887,622. It may also be in the form of a comb comprising a plurality of application members, obtained particularly by moulding. Such combs are described, for example, in patent FR 2 796 529. It may also be in the form of a brush comprising an arrangement of bristles of elastomeric material.

The applicator can be integral with the container, as described for example in patent FR 2 761 959. Advantageously, the applicator is integral with a stem, which for its part is integral with the closure element.

The applicator can optionally be provided with a rotary system. It can also comprise a heating device, or can be combined with a heating accessory. The closure element can be coupled to the container by screwing. Alternatively, the coupling between the closure element and the container takes place other than by screwing, especially via a bayonet mechanism, by click-fastening or by clamping. By "click-fastening" is meant in particular any system involving the crossing of a flange or bead of material by elastic deformation of a portion, especially of the closure element, followed by a return to the elastically non-constrained position of the said portion after the flange or bead has been crossed.

The container may be at least partly made of thermoplastic material. Examples of thermoplastic materials that can be mentioned are polypropylene and polyethylene. Alternatively, the container can be made of non-thermoplastic material, especially of glass or metal (or alloy).

The container is preferably equipped with a drainer located in the vicinity of the opening of the container. Such a drainer makes it possible to wipe the applicator and, optionally, the stem with which it can be integral. Such a drainer is described, for example, in patent FR 2 792 618.

The examples which follow are presented by way of illustration and do not limit the invention. The quantities indicated are percentages by weight and expressed relative to the total weight of the composition, unless otherwise indicated.

EXAMPLES

A—Examples of Compositions

Example 1

Comparison Example

| INCI NAME | Percentage |
| --- | --- |
| PARAFFIN | 12.00% |
| CARNAUBA | 3.00% |
| RICE BRAN WAX | 1.00% |
| STEARIC ACID & PALMITIC ACID | 7.50% |
| CERA ALBA | 3.50% |
| DIMETHICONE | 0.25% |
| PROPYLPARABEN | 0.20% |
| IRON OXIDES | 8.00% |
| WATER | QSF100 |
| METHYLPARABEN | 0.20% |
| PHENOXYETHANOL | 0.50% |
| ACACIA | 3.02% |
| POLYQUATERNIUM-10 | 0.10% |
| HYDROXYETHYLCELLULOSE | 0.84% |
| TRIETHANOLAMINE | 2.50% |
| AMINOMETHYLPROPANEDIOL | 0.50% |

Procedure for Example 1

The oily phase composed of the waxes is melted and homogenized towards 95° C. The pigment is then dispersed in this phase thanks to a strong shear. The aqueous phase is heated to 85° C. Saponification is carried out using a Stephan mixer by adding the oily phase to the aqueous phase accompanied by stirring. The composition is then cooled slowly to ambient temperature accompanied by stirring.

Applied to the eyelashes, the mascara gives a non-uniform result, in particular after coats are applied one on top of another.

Example 2 According to the Invention

| INCI NAME | Percentage |
| --- | --- |
| PARAFFIN | 12.00% |
| CARNAUBA | 2.25% |
| RICE BRAN WAX | 1.00% |
| STEARIC ACID & PALMITIC ACID | 7.50% |
| CERA ALBA | 3.50% |
| ETHYLENE/VA COPOLYMER & CERA MICROCRISTALLINA & SYNTHETIC WAX | 0.75% |
| DIMETHICONE | 0.25% |
| PROPYLPARABEN | 0.20% |
| IRON OXIDES | 8.00% |
| WATER | QSF100 |
| METHYLPARABEN | 0.20% |
| PHENOXYETHANOL | 0.50% |
| ACACIA | 3.02% |
| POLYQUATERNIUM-10 | 0.10% |
| HYDROXYETHYLCELLULOSE | 0.84% |
| TRIETHANOLAMINE | 2.50% |
| AMINOMETHYLPROPANEDIOL | 0.50% |

Procedure for Example 2

The oily phase composed of the waxes is melted and homogenized towards 95° C. The pigment is then dispersed in this phase thanks to a strong shear. The aqueous phase is heated to 85° C. Saponification is carried out using a Stephan mixer by adding the oily phase to the aqueous phase accompanied by stirring. The composition is then cooled slowly to ambient temperature accompanied by stirring.

This composition has a dry extract of 41% and an EVA/waxes ratio equal to 1:31.

The thus-obtained formulation has a texture which can be applied smoothly to the eyelash giving a good uniform, separating, lengthening and curling result.

It was noted that the mascara gives good coverage and volumizes well while remaining sufficiently separating and uniform after the number of coats on the eyelash is increased.

Example 3 According to the Invention

| INCI NAME | Percentage |
| --- | --- |
| PARAFFIN | 12.00% |
| CARNAUBA | 1.50% |
| RICE BRAN WAX | 1.00% |
| STEARIC ACID & PALMITIC ACID | 7.50% |
| CERA ALBA | 3.50% |
| ETHYLENE/VA COPOLYMER & CERA MICROCRISTALLINA & SYNTHETIC WAX | 1.50% |
| DIMETHICONE | 0.25% |
| PROPYLPARABEN | 0.20% |
| IRON OXIDES | 8.00% |
| WATER | QSF100 |
| METHYLPARABEN | 0.20% |
| PHENOXYETHANOL | 0.50% |
| ACACIA | 3.02% |
| POLYQUATERNIUM-10 | 0.10% |
| HYDROXYETHYLCELLULOSE | 0.84% |

-continued

| INCI NAME | Percentage |
|---|---|
| TRIETHANOLAMINE | 2.50% |
| AMINOMETHYLPROPANEDIOL | 0.50% |

Procedure for Example 3

The oily phase composed of the waxes is melted and homogenized towards 95° C. The pigment is then dispersed in this phase thanks to a strong shear. The aqueous phase is heated to 85° C. Saponification is carried out using a Stephan mixer by adding the oily phase to the aqueous phase accompanied by stirring. The composition is then cooled slowly to ambient temperature accompanied by stirring.

This composition has an EVA/waxes ratio equal to 1:15.

The mascara obtained has a very good curling effect.

Example 4 According to the Invention

| INCI NAME | Percentage |
|---|---|
| PARAFFIN | 10.90 |
| STEARIC ACID & PALMITIC ACID | 7.30 |
| CERA ALBA | 3.45 |
| CARNAUBA | 2.75 |
| RICE BRAN WAX | 1.00 |
| ETHYLENE/VA COPOLYMER & CERA MICROCRISTALLINA & SYNTHETIC WAX | 0.75 |
| PROPYLPARABEN | 0.20 |
| DIMETHICONE | 0.30 |
| IRON OXIDES | 10.00 |
| NYLON 6 (fibres) 2 mm | 0.40 |
| NYLON 6 (fibres) 1 mm | 0.40 |
| WATER | 17.50 |
| METHYL PARABEN | 0.20 |
| HYDROXYETHYLCELLULOSE & WATER (0.8% hydroxyethylcellulose) | 25.00 |
| ACACIA GUM & WATER (3% gum arabic) | 6.00 |
| WATER | 5.00 |
| AMINOMETHYLPROPANEDIOL | 0.50 |
| TRIETHANOLAMINE | 2.50 |
| PHENOXYETHANOL | 0.50 |
| PANTHENOL | 0.35 |
| ACRYLATES COPOLYMER & WATER (1.5% acrylates copolymers) | 5.00 |

Procedure for Example 4

The oily phase (1) is prepared by heating all the elements of this phase:
paraffin/stearic acid & palmitic acid/cera alba/carnauba/rice bran wax/ethylene/va copolymer & cera microcristallina & synthetic wax/propylparaben/dimethicone at 85° C.

The pigment is then added and grinding carried out with the rotor stator for 25 nm.

The Nylon® fibres are then added. The reaction mixture is then mixed with a butterfly-type impeller.

The aqueous phase (2) is prepared by heating the water to 75° C., then the methyl paraben is dissolved and the hydroxyethyl cellulose gel added followed by gum arabic gel.

Just before the emulsion is produced, the water/aminomethylpropanediol/triethanolamine mixture is introduced into the oily phase. The emulsion is then produced by adding phase (2) to phase (1).

The mixture is cooled to 40° C. and phenoxyethanol/panthenol/(copolymer acrylates & water) are added successively. The cooling is continued and the mascara recovered at 30/32° C.

This composition has an EVA/waxes ratio equal to 1:43.

The thus-obtained formulation has a texture which can be applied smoothly to the eyelash giving a good uniform, separating, lengthening and curling result.

It was noted that the mascara gives good coverage and volumizes well while remaining sufficiently separating and uniform after the number of coats on the eyelash is increased.

Example 5 According to the Invention

| INCI name | Percentage |
|---|---|
| TRIETHANOLAMINE | 2.500000 |
| PHENOXYETHANOL | 0.500000 |
| CYCLOPENTASILOXANE & TRIMETHYLSILOXYSILICATE (including 4.5% trimethylsiloxysilicate) | 10.000000 |
| WATER | 16.400000 |
| METHYL PARABEN | 0.200000 |
| POLYQUATERNIUM-10 | 0.200000 |
| ACACIA GUM & WATER (including 3% gum arabic) | 6.000000 |
| WATER | 2.500000 |
| HYDROXYETHYLCELLULOSE (including 0.74% hydroxyethylcellulose) | 22.000000 |
| PARAFFIN | 15.000000 |
| STEARIC ACID & PALMITIC ACID | 7.500000 |
| CERA ALBA | 3.500000 |
| CARNAUBA | 3.000000 |
| ETHYLENE/VA COPOLYMER & CERA MICROCRISTALLINA (MICROCRYTALLINE WAX) & SYNTHETIC WAX | 1.000000 |
| CELLULOSE/IRON OXIDES/SILICA | 1.000000 |
| AMINOMETHYLPROPANEDIOL | 0.500000 |
| PROPYLPARABEN | 0.200000 |
| IRON OXIDES | 8.000000 |

Procedure for Example 5 According to the Invention

The aqueous phase (phase 1) is prepared as follows: the water is heated to a temperature of 75° C. then the methyl paraben and then the polyquaternium-10 are dispersed, then the hydroxyethylcellulose gel and then the gum arabic gel are added.

The oily phase (3) is then prepared as follows: the mixture of waxes is heated to 85° C., then, when it is melted, the EVA copolymer and the pigment are added and grinding is carried out (rotor stator 30 nm). The cellulose/iron oxide/silica microbeads are then added.

A mixture of water, aminomethylpropanediol and triethanolamine is then prepared in order to obtain phase (2) which is introduced into the oily phase.

The emulsion is then produced. It is cooled to 40° C. and the remaining ingredients added.

The cooling is continued and the mascara recovered at 30/32° C.

This composition has an EVA/waxes ratio equal to 1:37.

The thus-obtained formulation has a texture which can be applied smoothly to the eyelash, giving a good uniform, separating, lengthening and curling result.

It was noted that the mascara gives good coverage and volumizes well while remaining sufficiently separating and uniform after the number of coats on the eyelash is increased.

Example 6 According to the Invention

| INCI name | Percentage |
| --- | --- |
| WATER | 24.800000 |
| SODIUM CITRATE | 0.130000 |
| BENTONITE | 1.500000 |
| POLYVINYL ALCOHOL | 2.500000 |
| WATER | 14.200000 |
| BUTYLENE GLYCOL | 3.000000 |
| PEG-10 GLYCERYL STEARATE | 4.000000 |
| POLYGLYCERYL-2 TRIISOSTEARATE | 0.200000 |
| CARNAUBA | 4.000000 |
| POLYBUTENE | 2.000000 |
| STEARIC ACID & PALMITIC ACID | 1.000000 |
| DIMETHICONE | 2.000000 |
| SQUALANE | 0.500000 |
| CERA ALBA | 3.000000 |
| ETHYLENE/VA COPOLYMER & CERA MICROCRISTALLINA (MICROCRYTALLINE WAX) & SYNTHETIC WAX | 1.000000 |
| IRON OXIDE | 10.000000 |
| DIMETHICONE | 1.000000 |
| NYLON 6 fibre 2 mm | 1.000000 |
| NYLON 6 fibre 1 mm | 1.000000 |
| WATER | 0.200000 |
| AMINOMETHYLPROPANEDIOL | 0.200000 |
| ALCOHOL | 2.000000 |
| METHYL PARABEN | 0.270000 |
| PHENOXYETHANOL | 0.500000 |
| STYRENE/ACRYLATES/AMMONIUM METHACRYLATE COPOLYMER & BUTYLENE GLYCOL & SODIUM LAURETH-12 SULPHATE | 20.000000 |

Procedure for Example 6

The aqueous phase is prepared:

the bentonite is dispersed in the water and sodium citrate.

separately, the poly(vinyl alcohol) is dispersed at 70° C. in the water, then cooled to 50° C. for incorporation into the production tank.

separately, the butylene glycol and the emulsifiers are heated to 50° C. to form a phase which is incorporated into the production tank.

The whole aqueous phase is then heated to 85° C.

The oily phase is then prepared: the waxes, the oils and the EVA copolymer are heated to 85° C. and the iron oxide is dispersed therein. The dimethicone is introduced.

The emulsion is then prepared by incorporating the oily phase into the aqueous phase. The temperature is reduced to 65-70° C. and the Nylon® fibres are introduced. The aminomethyl propanediol is then introduced into the water. The temperature is reduced to 40° C. and the alcohol and the preservatives are introduced. The temperature is reduced to 30° C. and the acrylic copolymer introduced.

This composition has an EVA/waxes ratio equal to 1:9. The thus-obtained formulation has a texture which can be applied smoothly to the eyelash, giving a good uniform, separating, lengthening and curling result.

Example 7 According to the Invention

| INCI name | Percentage |
| --- | --- |
| ETHYLENE/VA COPOLYMER & CERA MICROCRISTALLINA (MICROCRYTALLINE WAX) & SYNTHETIC WAX | 2.50% |
| CERA ALBA | 3.50% |
| PARAFFIN | 12.00% |
| STEARIC ACID & PALMITIC ACID | 7.50% |
| CARNAUBA | 1.50% |
| RICE BRAN WAX | 1.00% |
| PROPYL PARABEN | 0.20% |
| DIMETHICONE | 0.25% |
| IRON OXIDE | 8.00% |
| WATER | 26.85% |
| METHYL PARABEN | 0.20% |
| PHENOXYETHANOL | 0.50% |
| ACACIA | 6.00% |
| POLYQUATERNIUM-10 | 2.00% |
| HYDROXYETHYLCELLULOSE | 25.00% |
| TRIETHANOLAMINE | 2.50% |
| AMINOMETHYLPROPANEDIOL | 0.50% |

This composition was prepared similarly to the composition of Example 2. The weight ratio of the EVA copolymer to the waxes was 1:9.

B—Sensory Tests

1—Procedure for Sensory Tests

Tests were conducted on the mascara compositions of Examples 1 and 2.

Mascara compositions were each packaged in a small mascara bottle provided with an applicator (brush, comb, with or without reservoir).

A sensory analysis was carried out under standardized conditions (controlled temperature, hygrometry and light).

The procedure was as follows:

24 panel subjects participated in the construction of the sensory profile of the mascara composition. Each of the products was applied at the rate of 10+10 coats to the eyelashes of the panelists. 10 coats were added, then a further 10 coats, making a total of 40 coats. Each descriptor was rated on a continuous scale from 0 to 10.

2—Results of the Sensory Tests

The results of the comparative experiments conducted on Compositions 1 and 2 are given in the following table:

| | Comparison example 1 | Example 2[1] |
| --- | --- | --- |
| Coverage | 7.8 | +0.2 |
| Volume | 7.7 | +0.1 |

Definitions:
Coverage: capacity to cover the eyelashes over their whole length, eithout breaks.
Volume: ability of the product to increase the thickness and volume of the eyelashes.
[1]Difference relative to the comparison example.

Thus, the sensory analysis after addition of 40 coats suggested that the mascara composition of Example 2 gave more volume and better uniformity on the eyelash than the mascara composition of comparison example 1.

The invention claimed is:

1. A mascara composition comprising:
   a cosmetically acceptable aqueous medium; and
   an oily phase, said oily phase comprising at least one ethylene/vinyl acetate copolymer, and at least one wax or a mixture of waxes, wherein the weight ratio of the ethylene/vinyl acetate copolymer to the wax or mixture of waxes is comprised between 1:55 and 1:9.

2. The composition according to claim 1, wherein the ethylene/vinyl acetate copolymer is based only on ethylene and vinyl acetate monomers.

3. The composition according to claim 1, wherein the vinyl acetate content present in the copolymer is comprised between 5% and 55% by weight, relative to the total weight of the copolymer.

4. The composition according to claim 1, wherein the weight ratio of the ethylene/vinyl acetate copolymer to the wax or mixture of waxes is comprised between 1:55 and 1:15.

5. The composition according to claim 1, wherein the wax or the waxes are present in a total content ranging from 5 to 50% by weight, relative to the total weight of the composition.

6. The composition according to claim 1, wherein the ethylene/vinyl acetate copolymer is predispersed in the wax or the waxes.

7. The composition according to claim 6, wherein the wax used for the predispersion of the copolymer is a mixture of waxes comprising 25% by weight of synthetic wax other than synthetic microcrystalline wax relative to the total weight of the mixture of waxes and 75% by weight of synthetic microcrystalline wax relative to the total weight of the mixture of waxes.

8. The composition according to claim 1, further comprising a cellulose polymer, which is selected from the group consisting of alkylcelluloses, hydroxyalkylcelluloses, carboxyalkylcelluloses and their mixtures.

9. The composition according to claim 1, further comprising an optionally modified film-forming polymer of natural origin selected from the group consisting of:
   gum arabic, guar gum, xanthan derivatives, karaya gum; alginates and carrageenins;
   shellac resin, sandarac gum, dammar resins, elemi gums, copal resins;
   deoxyribonucleic acid; and
   mucopolysaccharides.

10. The composition according to claim 1, further comprising at least one cationic polyquaternium film-forming polymer.

11. The composition according to claim 1, further comprising an additional film-forming polymer selected from the group consisting of radical synthetic polymers, polycondensate synthetic polymers, polymers of natural origin and their mixtures.

12. The composition according to claim 1, further comprising at least one anionic surfactant.

13. The composition according to claim 1, wherein the vinyl acetate content present in the copolymer is approximately 13% by weight relative to the total weight of the copolymer.

14. The composition according to claim 1, wherein the vinyl acetate content present in the copolymer is approximately 28% by weight relative to the total weight of the copolymer.

15. The composition according to claim 1, wherein the weight ratio of the ethylene/vinyl acetate copolymer to the wax or mixture of waxes is comprised between 1:50 and 1:20.

16. The composition according to claim 1, wherein the wax or the waxes are present in a total content ranging from 10 to 35% by weight, relative to the total weight of the composition.

17. The composition according to claim 6, wherein the waxes are selected from the group consisting of synthetic wax, microcrystalline wax and their mixture.

18. A method for the cosmetic care or make-up of eyelashes or eyebrows comprising the application to said eyelashes or eyebrows of a composition according to claim 1.

19. A method for providing a filling make-up for the eyelashes or eyebrows and/or a smooth and uniform deposition on said eyelashes or eyebrows, comprising the application to said eyelashes or eyebrows of a composition according to claim 1.

20. A method for curling the eyelashes, comprising the application to said eyelashes of a composition according to claim 1.

* * * * *